(12) United States Patent
Takata et al.

(10) Patent No.: US 8,476,066 B2
(45) Date of Patent: Jul. 2, 2013

(54) BACTERIA ANALYZER, BACTERIA ANALYZING METHOD AND COMPUTER PROGRAM PRODUCT

(75) Inventors: Rumi Takata, Kobe (JP); Yousuke Tanaka, Kobe (JP); Noriyuki Narisada, Akashi (JP); Junya Inoue, Kobe (JP)

(73) Assignee: Sysmex Corporation (JP)

( * ) Notice: Subject to any disclaimer, the term of this patent is extended or adjusted under 35 U.S.C. 154(b) by 773 days.

(21) Appl. No.: 12/459,897

(22) Filed: Jul. 8, 2009

(65) Prior Publication Data

US 2010/0047856 A1 Feb. 25, 2010

(30) Foreign Application Priority Data

Jul. 8, 2008 (JP) ................................ 2008-177546

(51) Int. Cl.
*C12M 1/34* (2006.01)
*C12M 3/00* (2006.01)

(52) U.S. Cl.
USPC ............................ 435/288.7; 435/34; 435/39

(58) Field of Classification Search
USPC .......................................... 435/34, 39, 286.7
See application file for complete search history.

(56) References Cited

U.S. PATENT DOCUMENTS

| 4,987,086 A | 1/1991 | Brosnan et al. | |
| 5,757,476 A * | 5/1998 | Nakamoto et al. | ............... 356/73 |
| 2004/0219627 A1 | 11/2004 | Kawashima | |
| 2005/0079569 A1* | 4/2005 | Kawashima | .................... 435/34 |

FOREIGN PATENT DOCUMENTS

EP   1136563 A2   9/2001

OTHER PUBLICATIONS

Office Action from counterpart Chinese Application No. 200910158521.9, dated Sep. 8, 2010, 13 pages.

* cited by examiner

*Primary Examiner* — Michael Hobbs
(74) *Attorney, Agent, or Firm* — Brinks Hofer Gilson & Lione

(57) ABSTRACT

The present invention is to present a bacteria analyzer comprising: a detector comprising: a light source for irradiating light on a measurement sample prepared from a specimen and a reagent; and a light receiving unit for receiving light generated by irradiating the light on the measurement sample from the light source; a scattergram data acquirer for acquiring scattergram data for generating a scattergram having information related to size of the bacteria contained in the specimen and fluorescence information generated by the bacteria as parameters; a bacteria number acquirer for acquiring number of bacteria contained in a plurality of regions on the scattergram for each region; and a form determiner for determining a form of the bacteria contained in the specimen.

6 Claims, 16 Drawing Sheets

FIG. 12

| REVIEW | | NO. | 1125-201 | |
|---|---|---|---|---|
| NOT VALIDATED | | | 2006/04/12 16:23:36 | |

MAIN | TIME SERIES | RESEARCH1 | RESEARCH 2 | O-FLAG

ANALYSIS PARAMETERS

| RBC | | 40.1 /μL | | 116.3 /HPF |
| WBC | | 216.6 /μL | | 628.1 /HPF |
| EC | | 47.1 /μL | | 136.6 /HPF |
| CAST | | 0.00 /μL | | 0.00 /LPF |
| BACT | | 5857.0 /μL | | 5.9x10⁶ /μL |

RESEARCH PARAMETERS

| X'TAL | | | | 0.0 /μL |
| YLC | | | | 0.0 /μL |
| SRC | | | | 43.4 /μL |
| PATH.CAST | | | | 0.0 /μL |
| MUCUS | | | | 0.38 /μL |
| SPERM | | | | 0.0 /μL |
| COND. | | | | 13.4 mS/cm |

FLAGGING PARAMETERS

| X'TAL |
| YLC |
| SRC |
| PATH.CAST |
| MUCUS |
| SPERM |

RESEARCH INFORMATION

STREPTOCOCCAL ?

REVIEW COMMENT

RBC — S_FSC / RBC-S_FSC
WBC — S_FSC / WBC-S_FSC
EC/CAST — S_FSC / BACT — S_FSC
S1 / S2 / S3 / BI 302a, 302f, 302b, 302d, 302c, 302e

BACTERIA ANALYZER, BACTERIA ANALYZING METHOD AND COMPUTER PROGRAM PRODUCT

RELATED APPLICATIONS

This application claims priority under 35 U.S.C. §119 to Japanese Patent Application No. 2008-177546 filed on Jul. 8, 2008, the entire content of which is hereby incorporated by reference.

FIELD OF THE INVENTION

The present invention relates to a bacteria analyzer for detecting bacteria in a specimen and determining the form thereof, a bacteria analyzing method, and a computer program product.

BACKGROUND

Detecting bacteria contained in a specimen and determining the form thereof is being carried out in the fields of clinical examination, food sanitation examination, and the like.

An agar culture method is generally known for a method of detecting bacteria and determining the form thereof. This is an examination method of applying a sample to agar media, and classifying a colony, which is formed through culturing the bacteria over a predetermined time, using a microscope by an observer. However, in the agar culture method, the processing is complicated as it is a manual method, and it takes time to determine the form of the bacteria as culturing is required.

Thus, a method of detecting bacteria with a particle measurement device such as flow cytometer and determining the form thereof has been proposed in recent years.

For instance, U.S. Patent Publication No. 2004/0219627 discloses, as a method of determining the form of the bacteria contained in urine, a bacteria measurement method of creating a scattergram with information on the size of the bacteria and fluorescence information as parameters, analyzing the distribution state of the bacteria on the scattergram, calculating the tilt of a collection of particles from the distribution state of the particles of the entire scattergram, and determining whether the form of the bacteria in the specimen is a rod-shaped bacteria or a coccus based on the calculated tilt.

However, only the bacteria of a single form may not necessarily exist in the specimen, and the bacteria of different forms such as rod-shaped bacteria, chain coccus, and staphylococcal may exist in plurals. In such case, it is difficult to determine the form of the bacteria with the bacteria measurement method disclosed in U.S. Patent Publication No. 2004/0219627.

SUMMARY OF THE INVENTION

The first aspect of the present invention is a bacteria analyzer for analyzing bacteria contained in a specimen, comprising: a detector comprising: a light source for irradiating light on a measurement sample prepared from a specimen and a reagent; and a light receiving unit for receiving light generated by irradiating the light on the measurement sample from the light source; a scattergram data acquirer for acquiring scattergram data for generating a scattergram having information related to size of the bacteria contained in the specimen and fluorescence information generated by the bacteria as parameters, based on a signal obtained from the light received by the light receiving unit; a bacteria number acquirer for acquiring number of bacteria contained in a plurality of regions on the scattergram for each region, based on the scattergram data acquired by the scattergram data acquirer; and a form determiner for determining a form of the bacteria contained in the specimen, based on the number of bacteria in each region acquired by the bacteria number acquirer.

The second aspect of the present invention is a bacteria analyzer for analyzing bacteria contained in a specimen, comprising: a measurement device comprising: a light source for irradiating light on a measurement sample prepared from a specimen and a reagent; and a light receiving unit for receiving light generated by irradiating the light on the measurement sample from the light source; and a control device configured to perform operations comprising: (a) acquiring scattergram data for generating a scattergram having information related to size of the bacteria contained in the specimen and fluorescence information generated by the bacteria as parameters, based on a signal obtained from the light received by the light receiving unit; (b) acquiring number of bacteria contained in a plurality of regions on the scattergram for each region, based on the acquired scattergram data; and (c) determining a form of the bacteria contained in the specimen, based on the acquired number of bacteria in each region.

The third aspect of the present invention is a bacteria analyzing method for analyzing bacteria contained in a specimen, comprising steps of: (a) preparing a measurement sample from a specimen and a reagent; (b) irradiating light on the prepared measurement sample; (c) receiving light generated by irradiating the light on the measurement sample in the step (c); (d) acquiring scattergram data for generating a scattergram having information related to size of the bacteria contained in the specimen and fluorescence information generated by the bacteria as parameters, based on a signal obtained from the received light; (e) acquiring number of bacteria contained in a plurality of regions on the scattergram for each region, based on the acquired scattergram data; and (f) determining a form of the bacteria contained in the specimen, based on the acquired number of bacteria in each region.

The fourth aspect of the present invention is a computer program product for enabling a computer to analyze bacteria contained in a specimen, comprising: a computer readable medium; and software instructions, on the computer readable medium, for enabling the computer to perform operations comprising: (a) acquiring scattergram data for generating a scattergram having information related to size of the bacteria contained in a specimen and fluorescence information generated by the bacteria as parameters, based on a signal obtained from a light generated by irradiating light on a measurement sample prepared from the specimen and a reagent; (b) acquiring number of bacteria contained in a plurality of regions on the scattergram for each region, based on the acquired scattergram data; and (c) determining a form of the bacteria contained in the specimen, based on the acquired number of bacteria in each region.

BRIEF DESCRIPTION OF THE DRAWINGS

FIG. 12 shows an analysis result screen 302a displayed on the display unit 302 of the control device 3 of the bacteria analyzer 1 according to the first embodiment of the present invention;

DETAILED DESCRIPTION OF THE PREFERRED EMBODIMENTS

Figure 1:
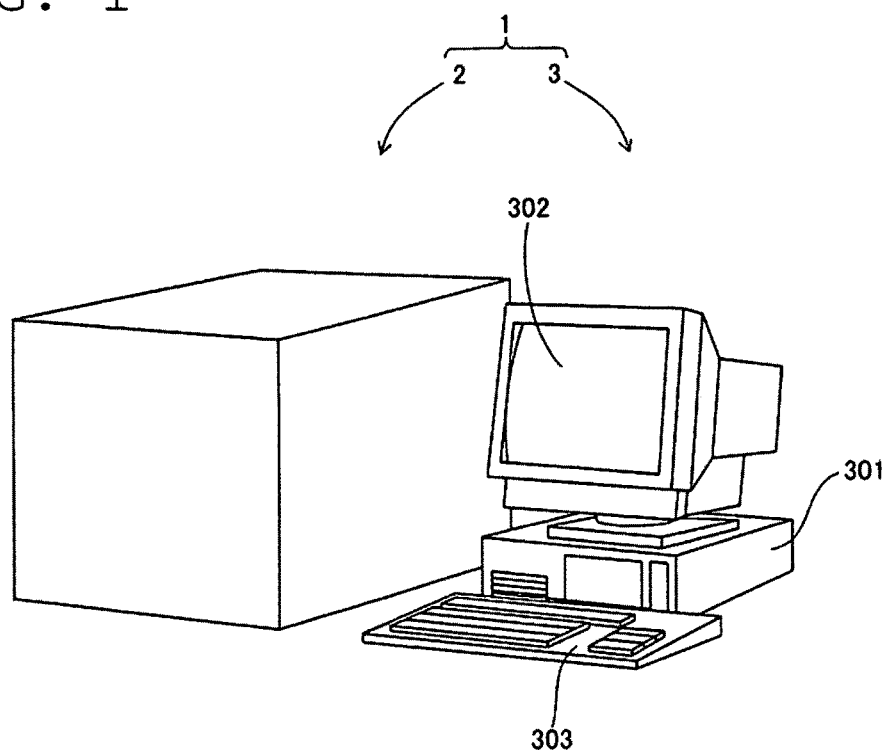
FIG. 1 is a schematic perspective view of a bacteria analyzer 1 according to a first embodiment of the present invention.

The present invention will be described based on the embodiments shown in the drawings. It should be recognized that the present invention is not limited thereby.

First Embodiment

A bacteria analyzer according to a first embodiment of the present invention is a device for counting the bacteria contained in a specimen (urine) based on the signals of forward scattered light and lateral fluorescence obtained by irradiating light on a measurement sample flowing through the flow cell, and determining the form of the bacteria contained in the specimen from the counted result. The bacteria contained in the specimen are classified by the form thereof, and classified into rod-shaped bacteria, coccus, and the like. The rod-shaped bacteria are bacteria in which the form is rod-shape or cylindrical. Although the size varies, the minor axis is generally about between 0.2 and 1 micrometer, and the major axis is about between 1 and 5 micrometer. The coccus is bacteria in which the form is a sphere. The coccus includes the chain coccus and the staphylococcal. The chain coccus is a coccus having a diameter of about one micrometer, and has individual fungus body aligned regularly in a straight chain. The staphylococcal is a coccus having a diameter of about one micrometer, and has individual fungus body aligned irregularly botryoidally.

As shown in FIG. 1, the bacteria analyzer 1 is configured by a measurement device 2 for optically measuring the bacteria contained in urine by a flow cytometer, and a control device 3 for analyzing the measurement result of the measurement device 2.

Figure 2:
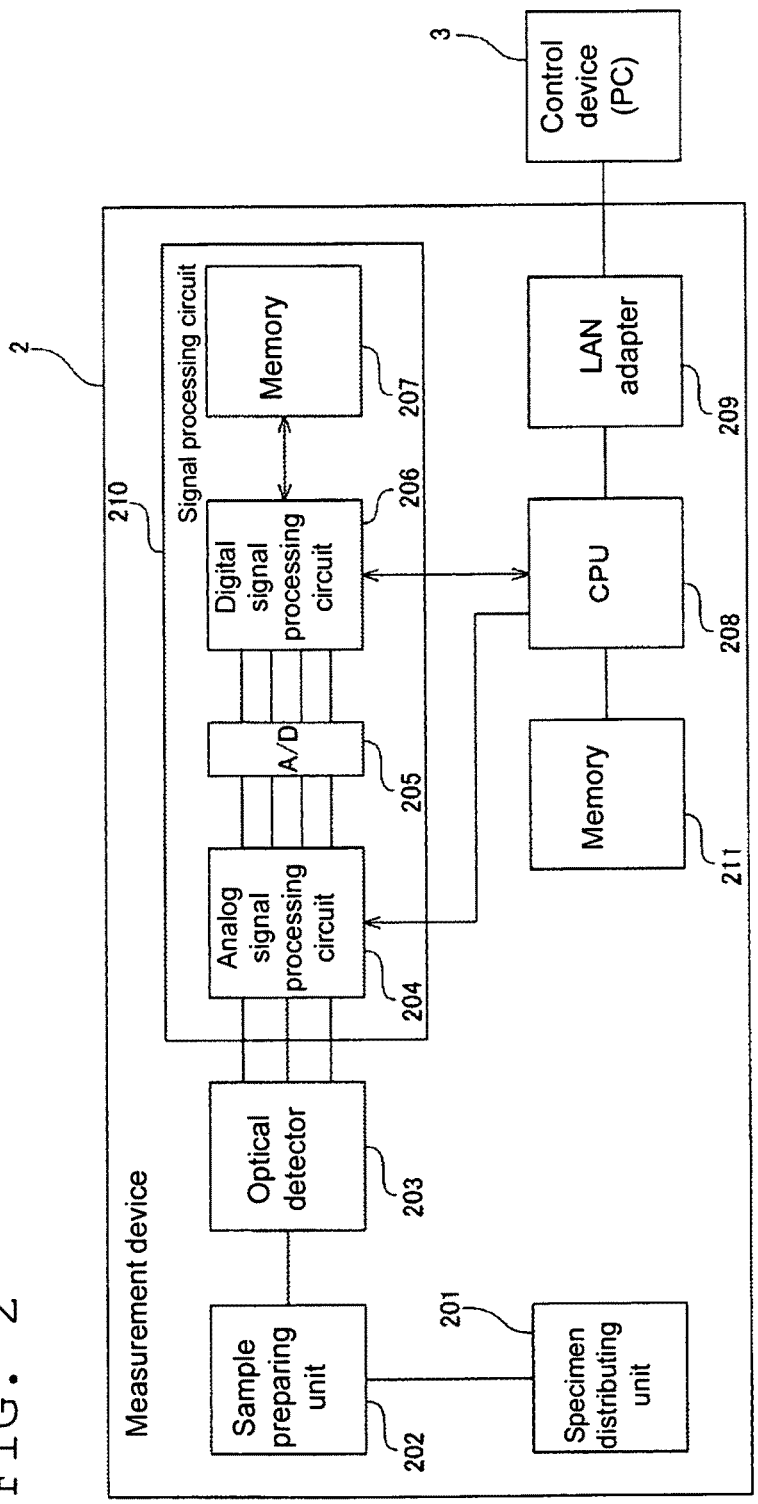
FIG. 2 is a block diagram showing a configuration of a measurement device 2 of the bacteria analyzer 1 according to the first embodiment of the present invention.

As shown in FIG. 2, the measurement device 2 includes a specimen distributing unit 201, a sample preparing unit 202, an optical detector 203, an analog signal processing circuit 204 for performing amplification of the output from the optical detector 203, an A/D converter 205 for converting the output of the analog signal processing circuit 204 to a digital signal, and a digital signal processing circuit 206 for performing a predetermined waveform processing on the digital signal. Furthermore, the measurement device 2 includes a memory 207 connected to the digital signal processing circuit 206, a CPU 208 connected to the analog signal processing circuit 204 and the digital signal processing circuit 206, and a LAN adapter 209 connected to the CPU 208. The measurement device 2 is connected to the control device 3 by way of the LAN adapter 209. A signal processing circuit 210 for an electrical signal output by the optical detector 203 is configured by the analog signal processing circuit 204, the A/D converter 205, the digital signal processing circuit 206, and the memory 207. The measurement device 2 includes a memory 211 including a BBURAM (Battery Backup RAM) and the like connected to the CPU 208.

The specimen distributing unit 201 includes a pipette and a pump for aspirating a predetermined amount of specimen (urine) into the pipette and discharging the aspirated specimen, and is configured to aspirate the predetermined amount of specimen from a specimen container and supply the same to the sample preparing unit 202.

The sample preparing unit 202 includes a mixing container (not shown) for preparing a measurement sample by mixing the specimen supplied by the specimen distributing unit 201, and a dilute solution and a staining fluid supplied from a reagent container (not shown), a pump for supplying the measurement sample prepared in the mixing container to a sheath flow cell 203c (see FIG. 3) of the optical detector 203, to be hereinafter described, along with the sheath solution, and the like. Here, UF II pack-BAC (manufactured by Sysmex Co.) can be used for the dilute solution, and UF II search-BAC (manufactured by Sysmex Co.) can be used for the staining fluid.

Figure 3:
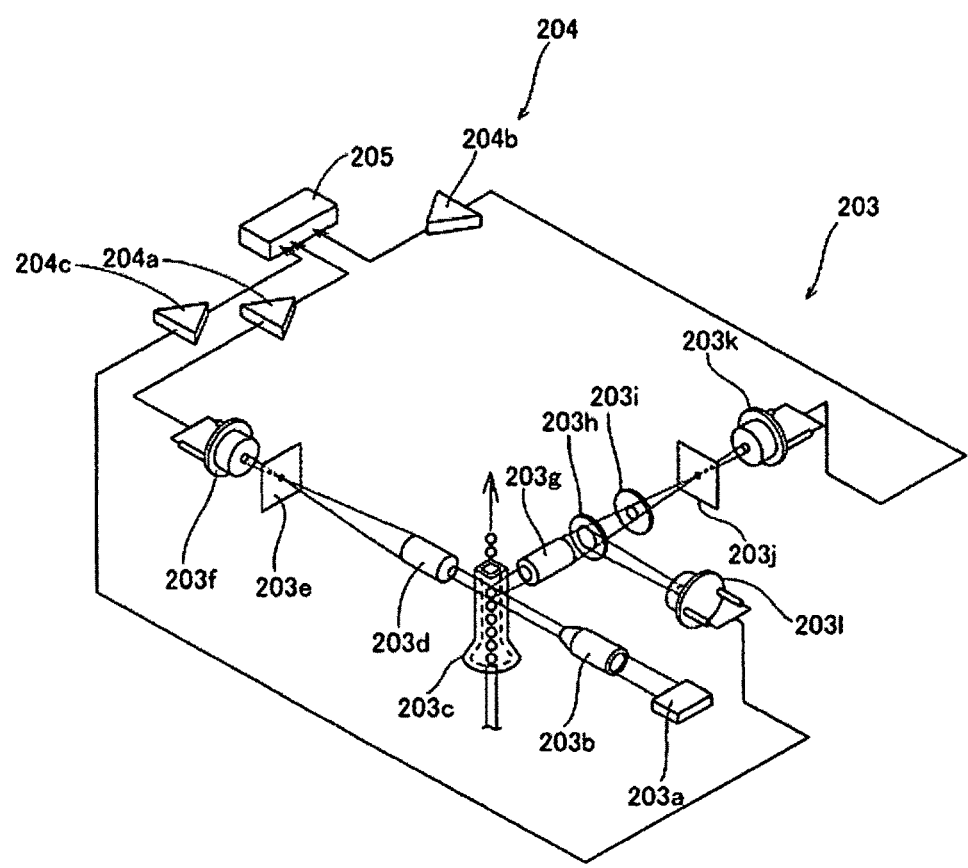
FIG. 3 is a schematic view showing a configuration of an optical detector 203 of the measurement device 2 of the bacteria analyzer 1 according to the first embodiment of the present invention.

FIG. 3 is a schematic view showing a configuration of the optical detector 203. As shown in FIG. 3, the optical detector 203 includes a light emitting unit 203a for emitting laser light, an irradiation lens unit 203b, a sheath flow cell 203c to which the laser light is irradiated, a light collecting lens 203d arranged on an extended line in a direction the laser light emitted from the light emitting unit 203a advances, a pin hole 203e and a photodiode (PD) 203f, a light collecting lens 203g arranged in a direction intersecting the direction the laser light emitted from the light emitting unit 203a advances, a dichroic mirror 203h, an optical filter 203i, a pin hole plate 203j including a pin hole and a photoelectron multiplier tube (PMT) 203k, and a photodiode (PD) 203l arranged at the side of the dichroic mirror 203h.

The light emitting unit 203a irradiates light on the sample flow containing the measurement sample that passes the interior of the sheath flow cell 203c. The irradiation lens unit 203b is provided to convert the light irradiated from the light emitting unit 203a to a parallel light. The PD 203f receives the forward scattered light generated from the sheath flow cell 203c.

The dichroic mirror 203h separates the lateral scattered light and the lateral fluorescence emitted from the sheath flow cell 203c. Specifically, the dichroic mirror 203h enters the lateral scattered light generated from the sheath flow cell 203c to the PD 203l, and enters the lateral fluorescence generated from the sheath flow cell 203c to the PMT 203k. The PD 203k and the PMT 203k respectively receive the lateral scattered light and the lateral fluorescence. The PD 203f, 203l and the PMT 203k can respectively convert the received light signal to an electrical signal.

As shown in FIG. 3, the analog signal processing circuit 204 includes amplifiers 204a, 204b, and 204c. The amplifiers 204a, 204b, and 204c respectively amplify the electrical signal output from the PD 203f, 203l, and the PMT 203k.

Returning to FIG. 2, the LAN adapter 209 is an Ethernet (registered trademark) interface, and the measurement device 2 can transmit and receive data with the control device 3 connected by way of a LAN cable by using a predetermined communication protocol (TCP/IP) by the LAN adapter 209.

The control device 3 is configured by a personal computer (PC), and the like. As shown in FIG. 1, the control device 3 includes a control unit 301, a display unit 302, and an input device 303. The control device 3 accepts the operation of the user, and can transmit an operation command to the measurement device 2. The control device 3 receives measurement data from the measurement device 2, processes the measurement data, and displays the analysis result.

Figure 4:
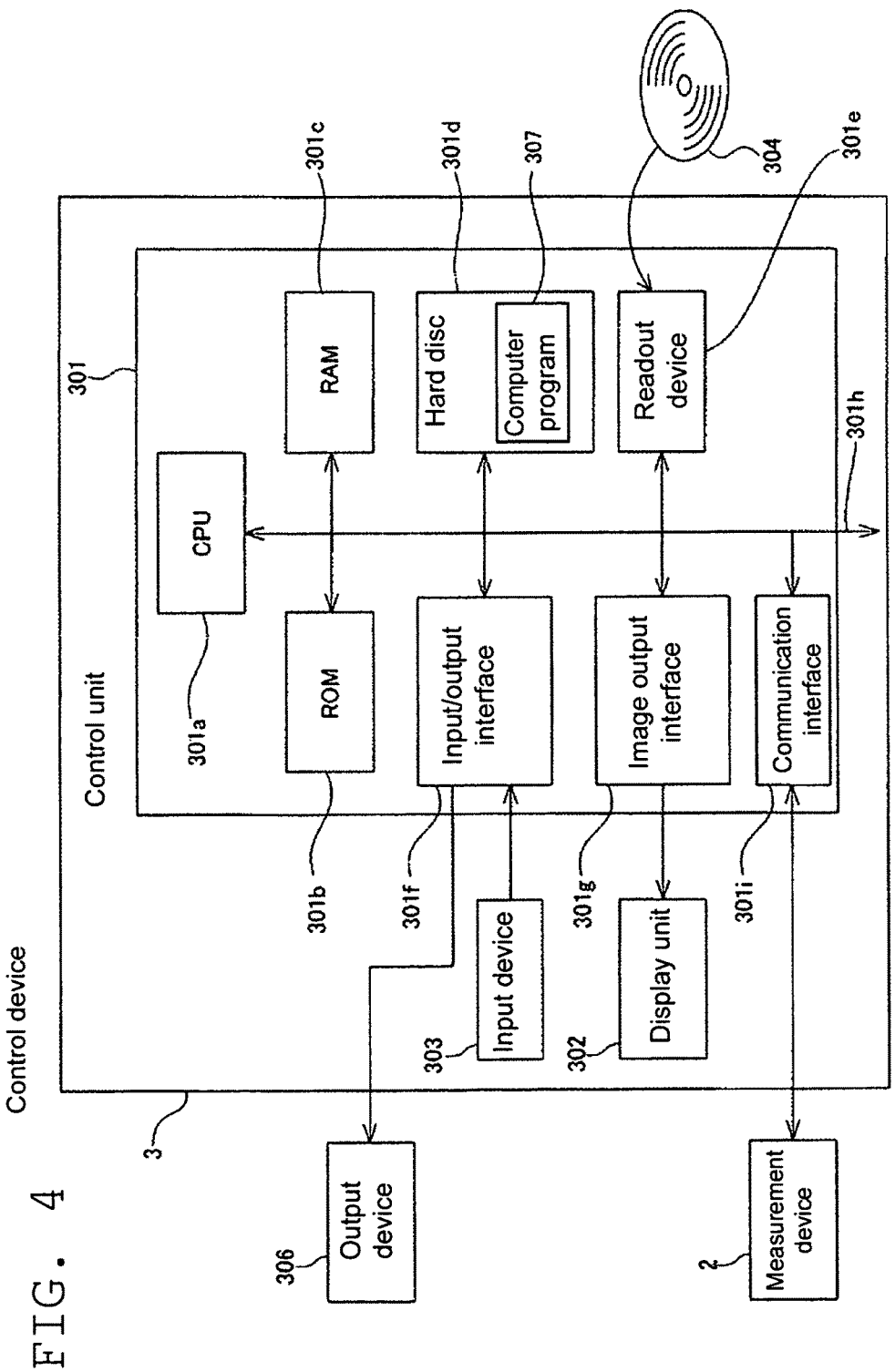
FIG. 4 is a block diagram showing a configuration of the control device 3 of the bacteria analyzer 1 according to the first embodiment of the present invention.

FIG. 4 is a block diagram showing a configuration of the control device 3. As shown in FIG. 4, the control unit 301 is configured by a CPU 301a, a ROM 301b, a RAM 301c, a hard disc 301d, a readout device 301e, an input/output interface 301f, an image output interface 301g, and a communication interface 301i. The CPU 301a, the ROM 301b, the RAM 301c, the hard disc 301d, the readout device 301e, the input/output interface 301f, the image output interface 301g, and the communication interface 301i are communicably connected to each other by a bus 301h.

The CPU 301a can execute the computer program stored in the ROM 301b and the computer program loaded to the RAM 301c. The personal computer functions as the control device 3 when the CPU 301a executes an analysis program 307 to be hereinafter described.

The ROM 301b is configured by mask ROM, PROM, EPROM, EEPROM, and the like. The ROM 301b stores the computer program executed by the CPU 301a, the data used when executing the computer program, and the like.

The RAM 301c is configured by SRAM, DRAM, or the like. The RAM 301c is used to read out the computer program stored in the ROM 301b and the hard disc 301d. The RAM 301c is used as a work region of the CPU 301a when executing such computer programs.

The hard disc 301d stores various computer programs to be executed by the CPU 301a, the data used therefor such as an operating system providing a graphical user interface environment such as Windows (registered trademark) manufactured and sold by U.S. Microsoft Co. and application program. The hard disc 301d also stores the analysis program 307 to be hereinafter described.

The readout device 301e is configured by flexible disc drive, CD-ROM drive, DVD-ROM, or the like. The readout device 301e can read out computer program or data stored in a portable storage medium 304, and the like. The portable storage medium 304 stores the analysis program 307. The CPU 301a controls the readout device 301e to read out the analysis program 307 from the portable storage medium 304, and can store the read out analysis program 307 in the hard disc 301d.

The input/output interface 301f is configured by serial interface such as USB, IEEE1394, RS-232C; parallel interface such as SCSI, IDE, IEEE1284; analog interface including D/A converter, A/D converter and the like.

The input device 303 including keyboard and mouse is connected to the input/output interface 301f. The user can use the input device 303 to input data to the control device 3. An output device 306 including a printer and the like is also connected to the input/output interface 301f.

The communication interface 301i is the Ethernet (registered trademark) interface. The control device 3 can transmit and receive data by using a predetermined communication protocol (TCP/IP) with the measurement device 2 connected by way of the LAN cable by means of the communication interface 301i.

The analysis program 307 is not limited to being provided to the control device 3 by the portable storage medium 304, and may be provided through an electrical communication line from an external device connected to the communication interface 301i by the electrical communication line (wired or wireless). For instance, the analysis program 307 may be stored in a hard disc of a server computer on the Internet, and the CPU 301a may access the server computer, download the analysis program 307 from the server computer, and store the same in the hard disc 301d.

The image output interface 301g is connected to the display unit 302 configured by LCD, CRT, or the like. The image output interface 301g outputs a video signal provided from the CPU 301a to the display unit 302. The display unit 302 displays an image (screen) based on the video signal input by the image output interface 301g.

Figure 5:
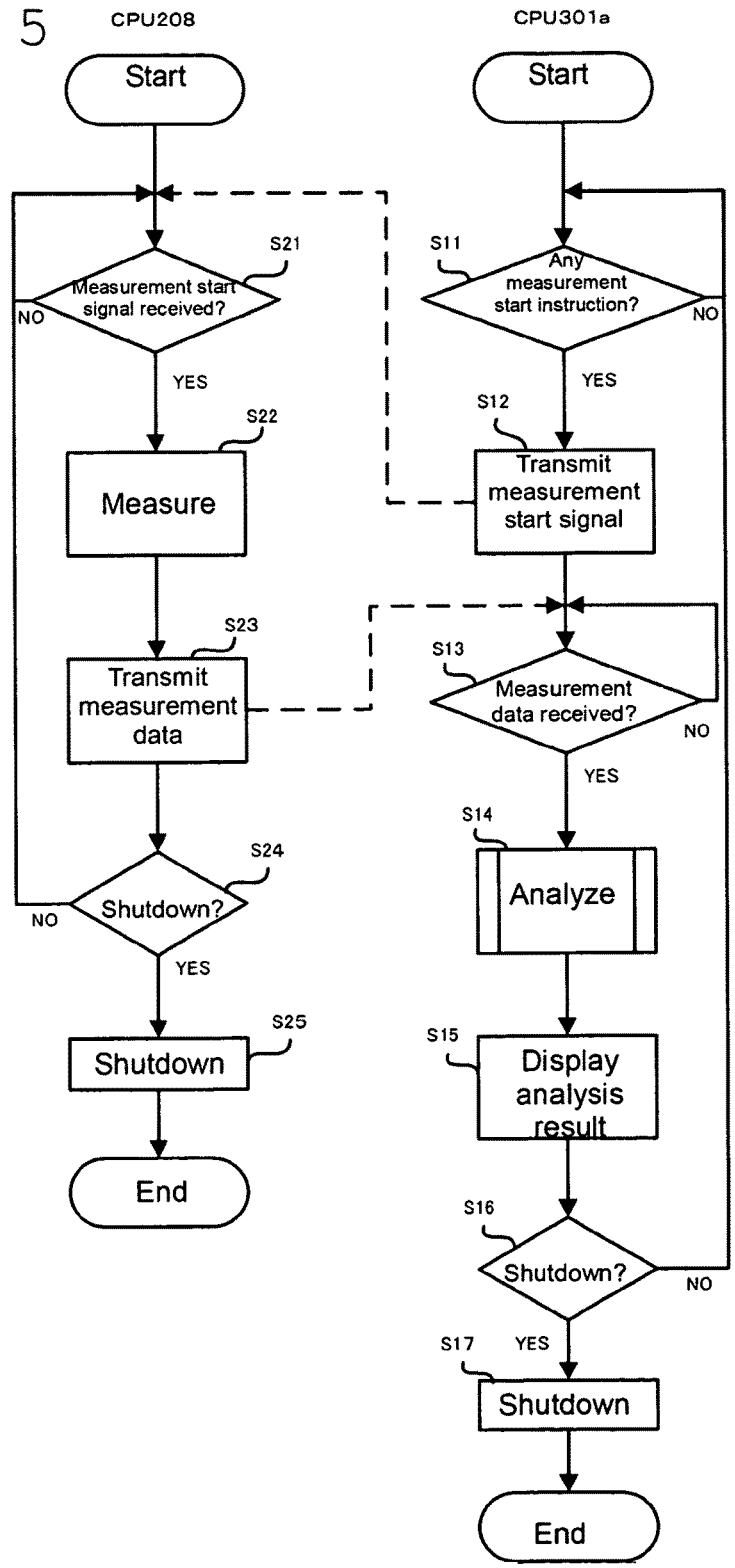
FIG. 5 is a flowchart showing the measurement process of the specimen by the CPU 208a of the measurement device 2 and the processing operation of the measurement result by the CPU 301a of the control device 3 of the bacteria analyzer 1 according to the first embodiment of the present invention.

FIG. 5 is a flowchart showing the flow of an analyzing process of a specimen by the CPU 208 and the CPU 301a. The specimen analyzing process of the bacteria analyzer 1 according to the present embodiment will be described with reference to FIG. 5.

First, the CPU 301a executes a process of waiting until a measurement start instruction from the operator is made (step S11). When the measurement start instruction is input from the operator (YES in step S11), the CPU 301a executes a process of transmitting the measurement start signal to the measurement device 2 (step S12).

The CPU 208 executes a process of waiting for the reception of the measurement start signal transmitted from the CPU 301a (step S21). When receiving the measurement start signal transmitted from the CPU 301a (YES in step S21), the CPU 208 executes a specimen measurement process (step S22).

In the measurement process of step S22, the CPU 208 first executes a process of controlling the specimen distributing unit 201 so as to aspirate the specimen from the specimen container, and supply the aspirated specimen to the sample preparing unit 202. The CPU 208 then executes a process of controlling the sample preparing unit 202 so as to prepare the measurement sample from the supplied specimen and the reagent (dilute solution and staining fluid) aspirated from the reagent container (not shown). The measurement sample prepared by the sample preparing unit 202 is supplied to the sheath flow cell 203c of the optical detector 203 along with the sheath liquid.

The CPU 208 then executes a process of controlling the light emitting unit 203a so as to irradiate light on the sample flow including the measurement sample flowing through the interior of the sheath flow cell 203c. When the sheath flow cell 203c is irradiated with light by the light emitting unit 203a, the forward scattered light, the lateral scattered light, and the lateral fluorescence exit from the measurement sample are received by the PD 203f, the PD 203l, and the PMT 203k.

The electrical signal generated by the light signal received by the PD 203f, the PD 203l, and the PMT 203k is amplified by the amplifiers 204a, 204b, and 204c, and converted to a digital signal by the A/D converter 205. The converted digital signal is performed with a predetermined waveform processing by the digital signal processing circuit 206, and stored in the memory 207. The digital signal stored in the memory 207 includes the pulse signal of the forward scattered light and the lateral fluorescence generated every time the bacteria passes through the sheath flow cell 203c.

The CPU 208 then executes a process of acquiring the height of the pulse signal of the forward scattered light and the lateral fluorescence from the digital signal stored in the memory 207. The height of the pulse signal of the forward scattered light indicates the intensity of the forward scattered light generated when one bacterium passes through the sheath flow cell 203c, and the height of the pulse signal of the lateral fluorescence similarly indicates the intensity of the lateral fluorescence generated when one bacterium passes through the sheath flow cell 203c. The height of the pulse signal of the forward scattered light reflects the size of the bacterium, and the height of the pulse signal of the lateral fluorescence reflects the staining degree of the nucleic acid contained in the bacterium.

After acquiring the height of the pulse signal of the forward scattered light and the lateral fluorescence, the CPU 208 executes a process of generating data group of the forward scattered light intensity and the lateral fluorescence intensity for each bacterium passed through the sheath flow cell 203 based on the acquired height of the pulse signal. This data group is hereinafter referred to as measurement data.

After the measurement process of the specimen is terminated, the CPU 208 executes a process of transmitting the measurement data to the control device 3 (step S23).

After executing the process of transmitting the measurement start signal, the CPU 301a executes a process of waiting for the reception of the measurement data transmitted from the CPU 208 (step S13). When receiving the measurement data transmitted from the CPU 208 (YES in step S13), the CPU 301a stores the received measurement data in the hard disc 301d, and then executes the analyzing process of the measurement data (step S14).

Figure 6:
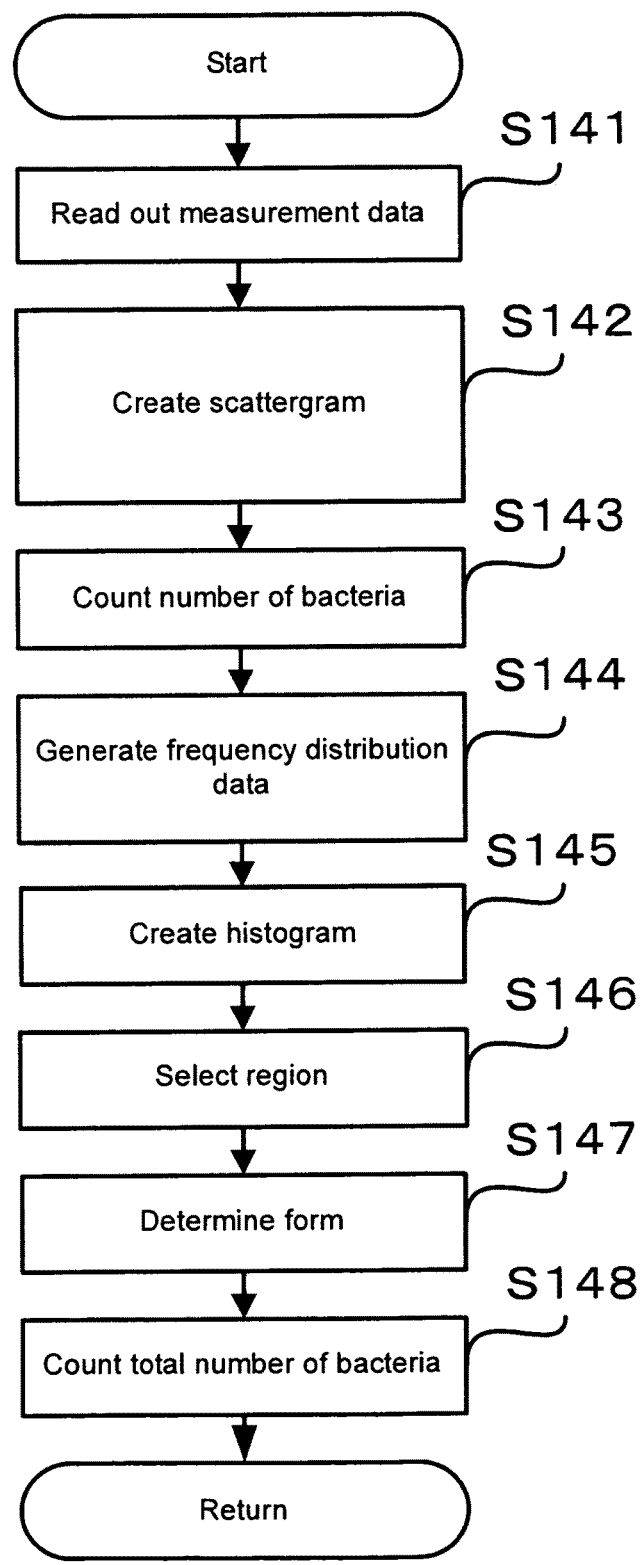
FIG. 6 is a flowchart showing a flow of the detailed process in step S14 of the flowchart shown in FIG. 5.

FIG. 6 is a flowchart of the analyzing process of the measurement data by the CPU 301a in step S14. The analyzing process of the measurement data by the CPU 301a will be described with reference to FIG. 6.

First, the CPU 301a executes a process of reading out the measurement data from the hard disc 301d to the RAM 301c (step S141).

Figure 7:
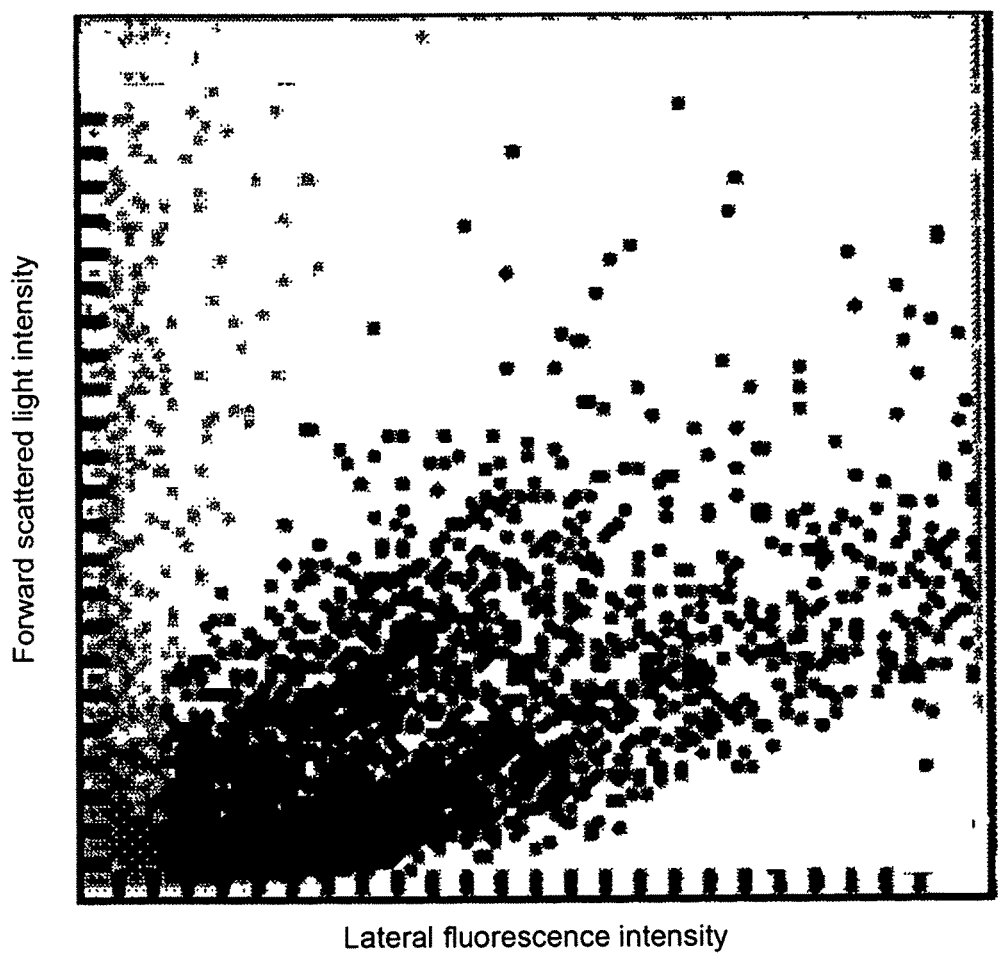
FIG. 7 shows a scattergram created by the process in step S142 of the flowchart shown in FIG. 6.

The CPU 301a then executes a process of creating a two-dimensional scattergram having the forward scattered light intensity on the vertical axis and the lateral fluorescence intensity on the horizontal axis based on the measurement data read out from the hard disc 301d to the RAM 301c in step S141 (step S142). Each of bacteria is plotted on a predetermined position on the two-dimensional scattergram depending on the forward scattered light intensity and the lateral fluorescence intensity thereof. FIG. 7 shows a scattergram created by the CPU 301a in step S1142 based on the measurement data acquired in the process of step S141.

Figure 8:
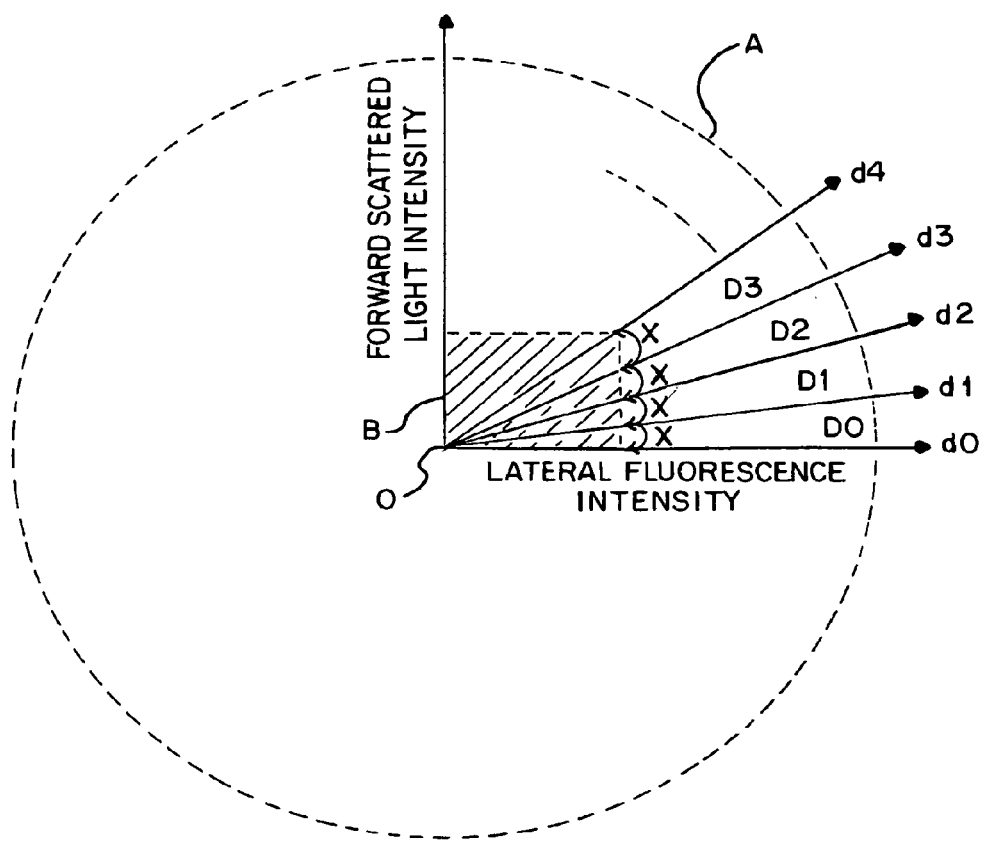
FIGS. 8 and 9 are schematic views of the scattergram for describing the process in step S143 of the flowchart shown in FIG. 6.

The CPU 301a then executes a process of counting the number of bacteria contained in a plurality of regions in the scattergram created in step S142 for the respective region (step S143). FIG. 8 is a schematic view of the scattergram created in step S142. As shown in FIG. 8, the plurality of regions in the scattergram are denoted as regions D0, D1, D2, D3, . . . . The regions D0, D1, D2, D3, . . . are regions divided in the radial directions d0, d1, d2, d3, d4, . . . of a virtual circle A having an origin O of the scattergram as the center. The regions D0, D1, D2, D3, . . . are divided for every angle X. X can be arbitrarily defined, and may be set to one degree or ten degrees.

The region B shown with hatching including the origin O is excluded from the regions D0, D1, D2, D3, . . . . The region B is excluded because the range of each region D0, D1, D2, D3, . . . is narrow in a region in which the forward scattered light intensity and the lateral fluorescence intensity are small compared to a region in which the forward scattered light intensity and the lateral fluorescence intensity are large. A more accurate counting of the bacteria is realized by excluding the region B from each region D0, D1, D2, D3, . . . .

Figure 9:
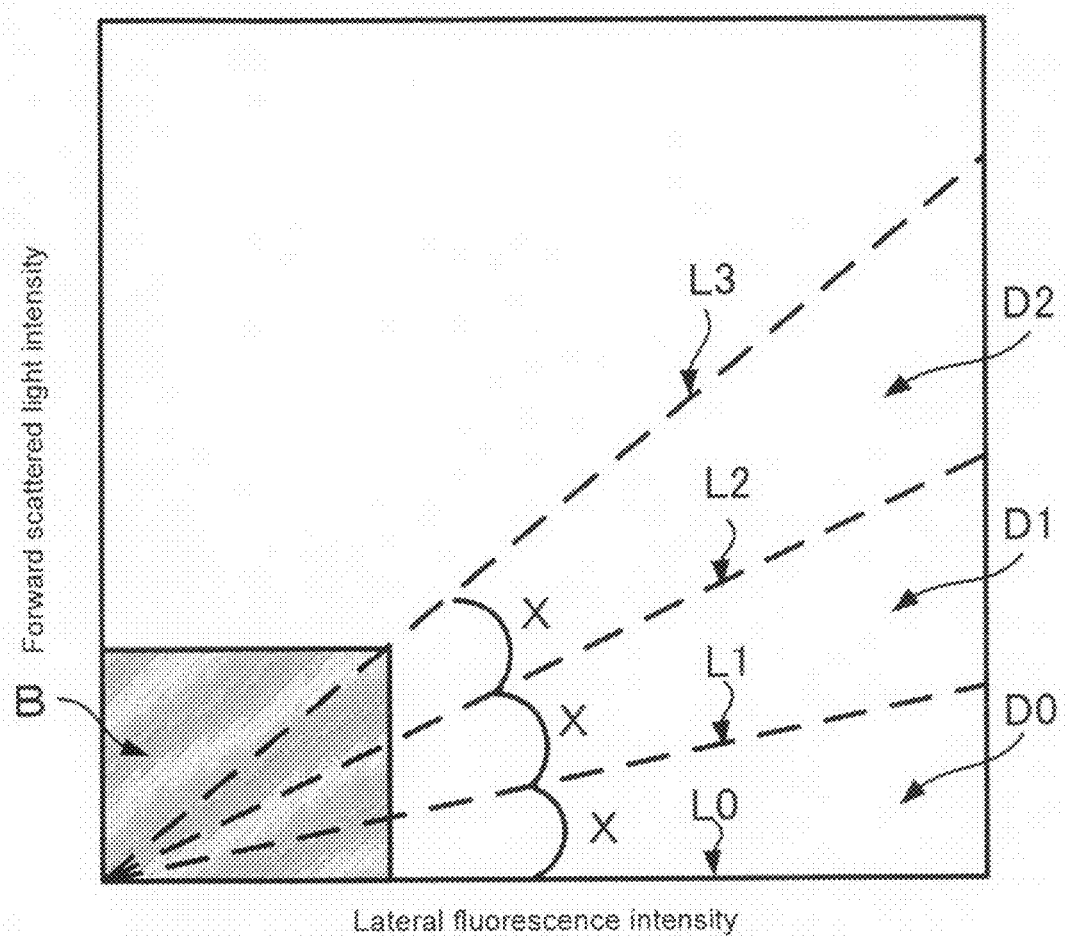

FIG. 9 is a schematic view of the scattergram created in step S142 similar to FIG. 8. Each region will be specifically described with reference to FIG. 9. In FIG. 9, each region is a region divided by the horizontal axis L0 and the virtual lines L1, L2, L3, . . . drawn on the scattergram. Here, the region D0 is a region sandwiched by the horizontal axis L0 and the line L1 tilted by an angle X from the horizontal axis L0 and excluded with the region B. The region D1 is a region sandwiched by the line L1 and the line L2 tilted by an angle X from the line L1 and excluded with the region B. The region D2 is a region sandwiched by the line L2 and the line L3 tilted by an angle X from the line L2 and excluded with the region B. The regions D3 . . . are similar to the regions D0, D1, and D2.

In other words, the regions D0, D1, D2, D3, . . . shown on the scattergram created in step S142 are regions divided at radially equal angle with the origin O of the scattergram as the center and excluded with the region B, as shown in FIGS. 8 and 9.

The CPU 301a then executes a process of generating frequency distribution graph data (step S144). The frequency distribution graph data generated in step S144 is a data group in which each region D0, D1, D2, D3, . . . and the number of bacteria contained in the respective region form a pair.

Figure 10:
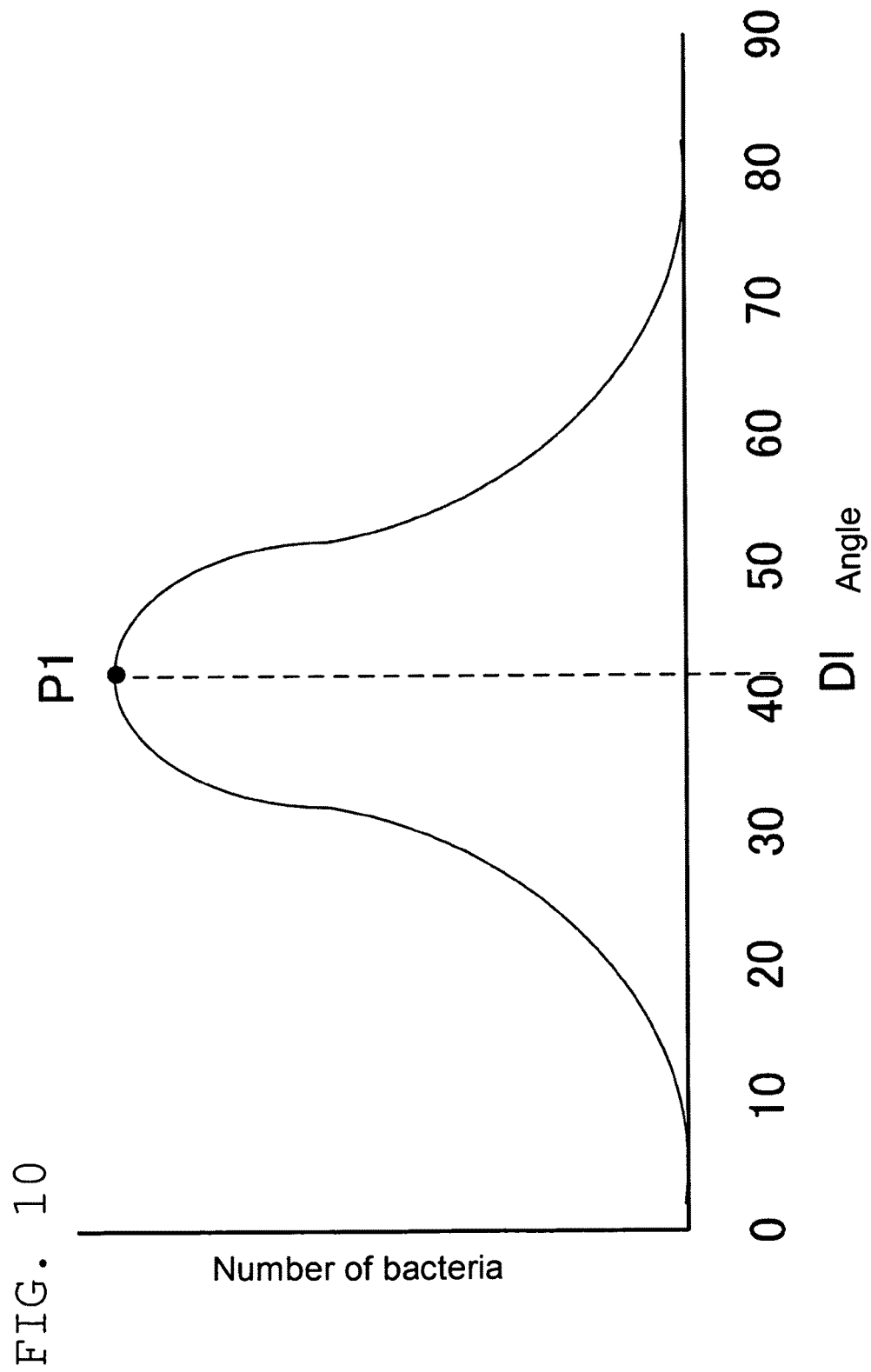
FIGS. 10 and 11 are examples of a histogram created by the process in step S145 of the flowchart shown in FIG. 6.
Figure 11:
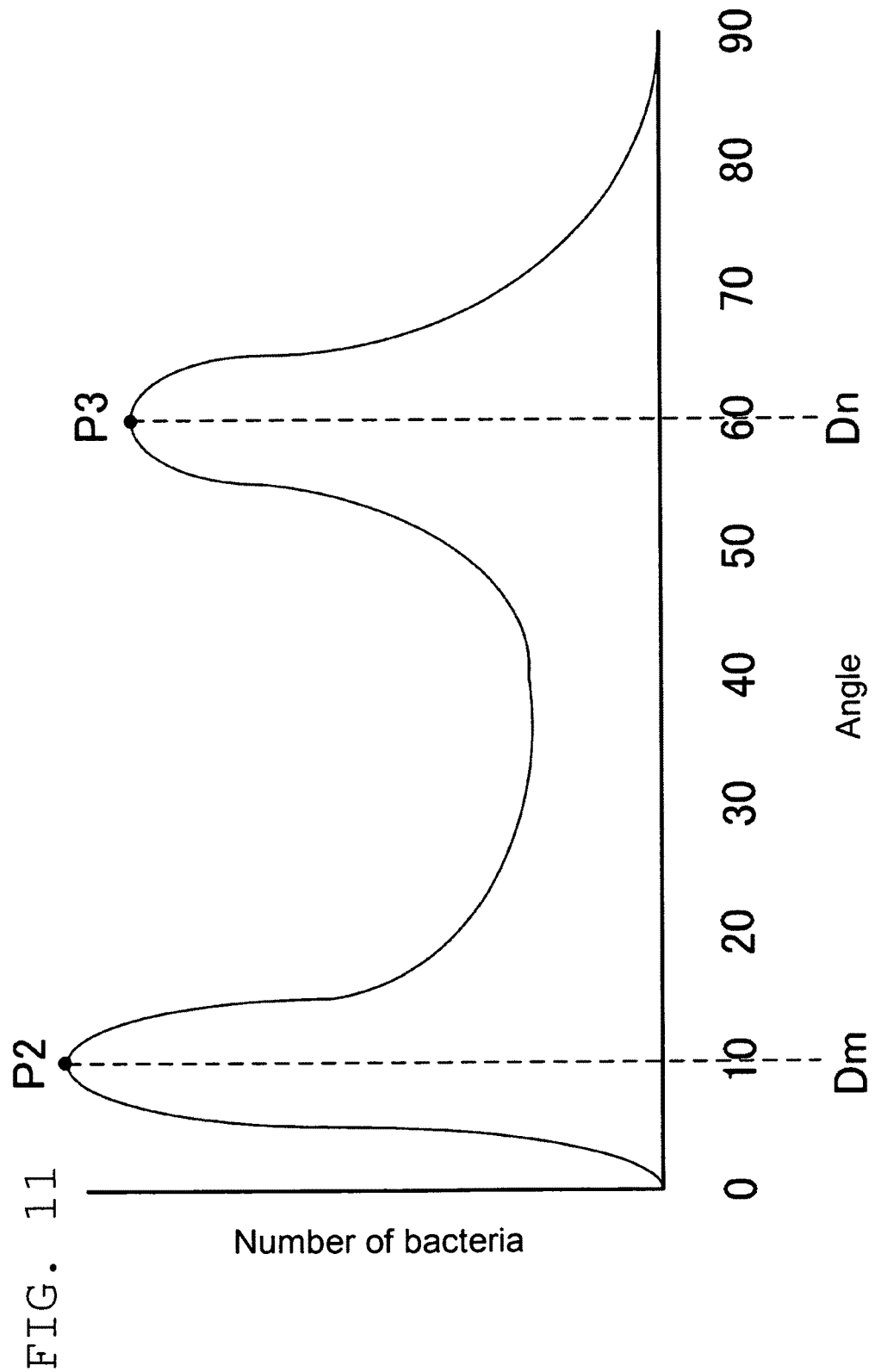

FIGS. 10 and 11 show examples of a histogram. The CPU 301a creates a histogram as shown in FIGS. 10 and 11 based on the frequency distribution graph data generated in step S144 (step S145). In the histogram, the horizontal axis shows the angle from the d0 direction of the directions d0, d1, d2, d3, d4, . . . dividing each region D0, D1, D2, D3, . . . . In other words, the horizontal axis is assigned each region D0, D1, D2, D3, . . . in order from the smallest, and corresponds to the distribution position of each region in the scattergram. The vertical axis of the histogram indicates the number of bacteria contained in each region D0, D1, D2, D3, . . . , that is, the number of bacteria counted in step S143.

The CPU 301a then executes a process of selecting a region based on the histogram created in step S145 (step S146). Specifically, a region where the number of bacteria is a peak in the histogram created in step S145 is selected. The region in which the number of bacteria is a peak is a region at the top of the histogram shown in FIGS. 10 and 11 where the number of bacteria contained therein is greater than the number of bacteria contained in each region adjacent on both sides on the scattergram shown in FIG. 8. For instance, in the histogram shown in FIG. 10, the peak of the number of bacteria is indicated as P1. In this case, the CPU 301a selects the region D1 in which the number of bacteria is peak P1. In the histogram shown in FIG. 11, the peak of the number of bacteria is indicated as P2 and P3. In this case, the CPU 301a selects a region Dm in which the number of bacteria is peak P2 and a region Dn in which the number of bacteria is peak P3.

The peak to be selected herein may be set to one or plurals. If the peak to be selected is set to one, one type of the form of bacteria is determined by the CPU 301. If the peak to be selected is set to plurals, the plural types of the forms of bacteria are determined by the CPU 301a.

The CPU 301a then executes a process of determining the form of bacteria based on the region selected in step S146 (step S147). In this process, the CPU 301a determines the form of bacteria by the angle from the direction d0 of the directions d0, d1, d2, d3, d4, ... dividing the selected region. Which angle to assign to which form of bacteria can be defined based on experimental data, and low angle region (e.g., 0 degree to 25 degrees) may be assigned to the rod-shaped bacteria, intermediate angle region (e.g., 25 degrees to 45 degrees) may be assigned to chain coccus, and high angle region (e.g., 45 degrees to 80 degrees) may be assigned to staphylococcal.

If assigned in such matter, the CPU 301a executes the process of determining that the chain coccus is contained in the specimen since the angle from the d0 direction of the direction dividing the selected region D1 is about 40 degrees in the histogram shown in FIG. 10. The CPU 301a executes the process of determining that the rod-shaped bacteria and the staphylococcal are contained in the specimen since the angle from the d0 direction of the direction dividing the selected region Dm is about 10 degrees and the angle from the d0 direction of the direction dividing the selected region Dn is about 60 degrees in the histogram shown in FIG. 11.

The CPU 301a then executes a process of counting the total number of bacteria contained in the specimen based on the measurement data acquired in S141 (step S148).

Returning to FIG. 5, the CPU 301a executes a process of controlling the display unit 302 so as to display an analysis result screen 302a showing the total number of bacteria counted in step S14 and the determined form of bacteria (step S15).

FIG. 12 shows the analysis result screen 302a showing the result of the analyzing process executed by the CPU 301a in step S14. As shown in FIG. 12, the analysis result screen 302a includes a counted result display region 302b, a scattergram display region 302c, and a form display region 302d. In the counted result display region 302b, the total number of bacteria 302f counted in step S148 (see FIG. 6) is displayed along with the counted result of other analyzing items. In the scattergram display region 302c, the scattergram 302e created in step S142 (see FIG. 6) is displayed along with the scattergram of other analyzing items. In the form display region 302d, the form of bacteria determined in step S147 (see FIG. 6) is displayed. The analysis result screen 302a shown in FIG. 12 is an example of the case of being determined that the form of bacteria is chain coccus. When the form of bacteria is determined, a display suggesting the presence of the relevant bacteria may be made as in the present embodiment or a display asserting the presence of the relevant bacteria may be made.

After executing the process of step S15, the CPU 301a executes a process of determining whether or not to execute a shutdown process (step S16). When determined to execute the shutdown process (YES in step S16), the CPU 301a executes the shutdown process (step S17). When determined not to execute the shutdown process (NO in step S16), the CPU 301a executes the process of step S11.

After executing the process of step S23, the CPU 208 executes a process of determining whether or not to execute the shutdown process (step S24). When determined to execute the shutdown process (YES in step S24), the CPU 208 executes the shutdown process (step S25). When determined not to execute the shutdown process (NO in step S24), the CPU 208 executes the process of step S21.

Second Embodiment

Figure 13:
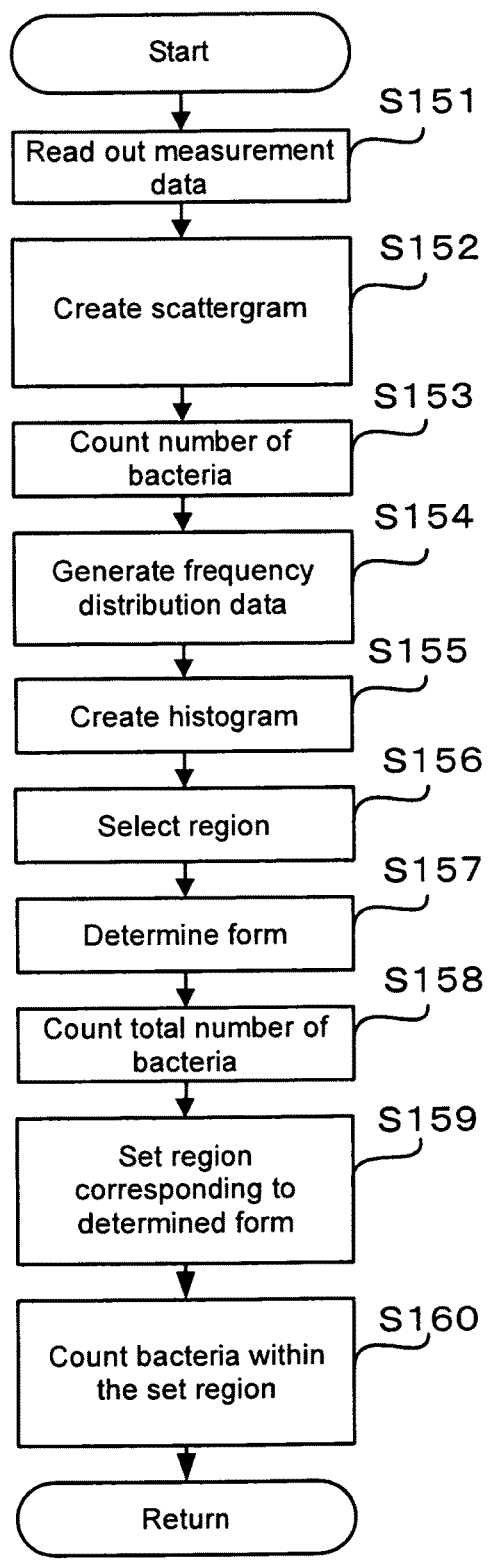
FIG. 13 is a flowchart showing the processing operation of the measurement result by the CPU 301a of the control device 3 of the bacteria analyzer 1 according to a second embodiment of the present invention.

A bacteria analyzer according to a second embodiment will now be described. The bacteria analyzer according to the second embodiment differs from the bacteria analyzer according to the first embodiment only in counting the bacteria belonging to the determined form, and is the same in other aspects. FIG. 13 is a flowchart showing a detailed flow of the process in step S14 of the CPU 301a of the control device 3 in the bacteria analyzer 1 according to the second embodiment. The processes in steps S151 to 158 are the same as the processes in steps S141 to S148 (see FIG. 6), and thus the description will be omitted.

Figure 14:
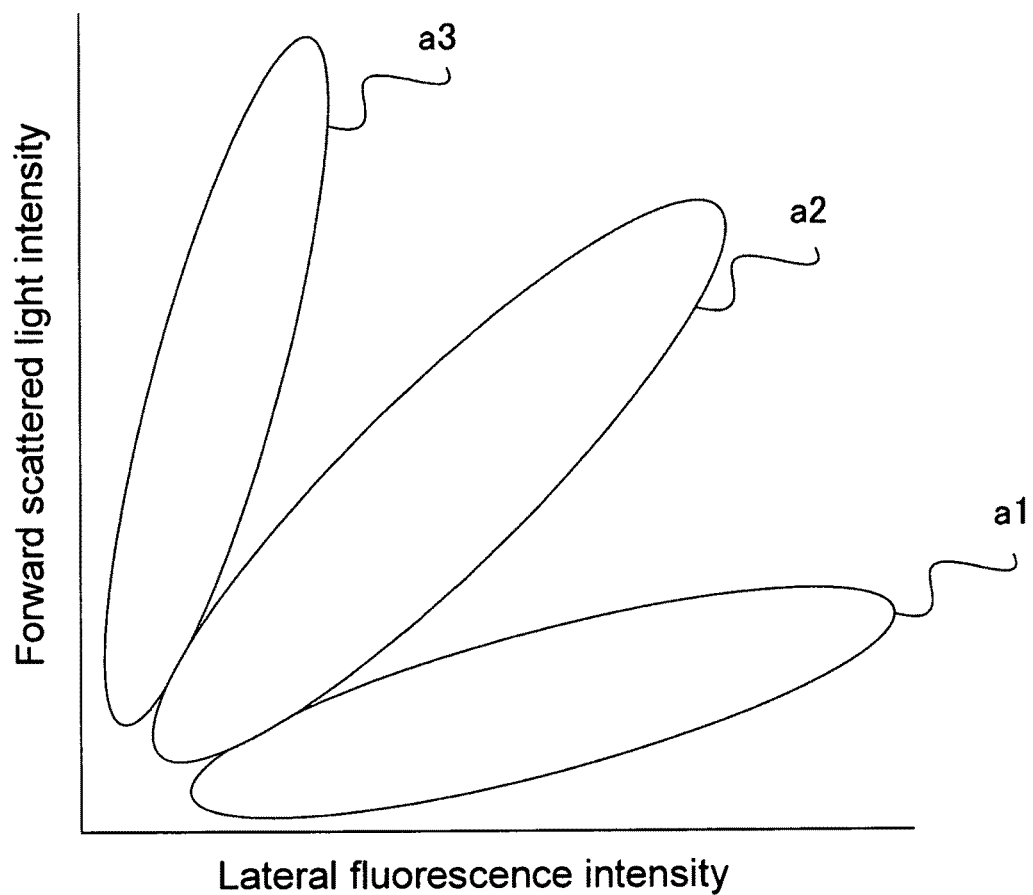
FIG. 14 is a schematic view of a scattergram for describing region setting for counting the bacteria of every form by the CPU 301a of the control device 3 of the bacteria analyzer 1 according to the second embodiment of the present invention.

FIG. 14 is a schematic view of a scattergram. After executing the process of step S158, the CPU 301a sets a region a1, a2, or a3, as shown in FIG. 14, depending on the form determined in step S157 (step S159). The regions a1 to a3 may be stored in the RAM 301c, the hard disc 301d, and the like in advance, or may be set by the CPU 301a depending on the distribution state of the bacteria on the scattergram. The CPU 301a sets the region a1 when the determined form is the rod-shaped bacteria, sets the region a2 when the determined form is the chain coccus, and sets the region a3 when the determined form is the staphylococcal. The CPU 301a sets a region for each form if the determined form is in plurals.

The CPU 301a then executes a process of counting the bacteria contained in the set region (step S160). The counted result indicates the number of bacteria belonging to the determined form. The CPU 301a counts the bacteria contained in the respective set region if the set region is in plurals. After executing the process in step S160, the CPU 301a executes a process of controlling the display unit 302 to display the analysis result screen 302a showing the counted number of bacteria belonging to a predetermined form in step S15 (see FIG. 6). In this case, the number of bacteria belonging to the determined form may be displayed in the counted result display region 302b or may be displayed in the form display region 302d.

Figure 15:
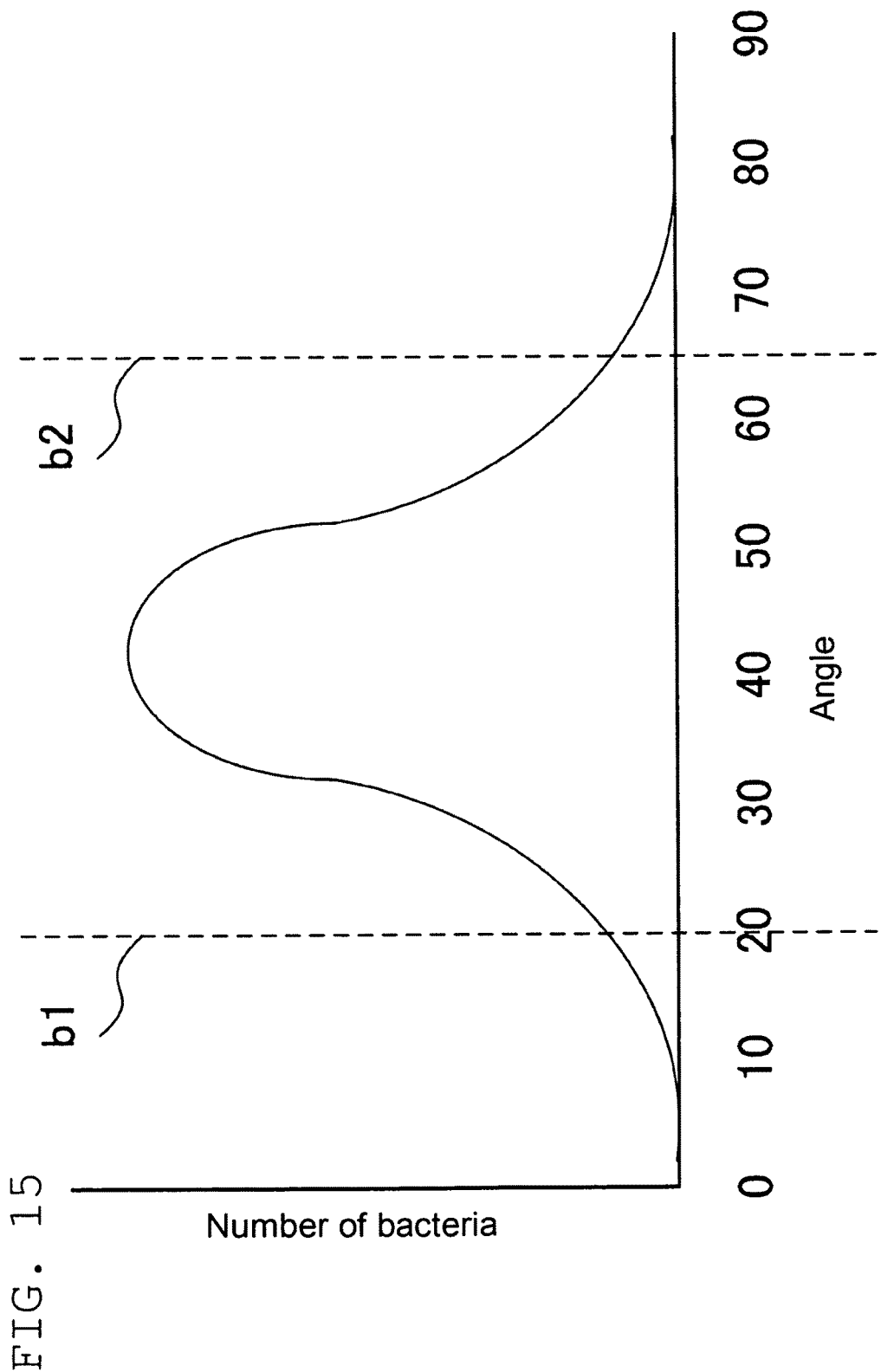
FIGS. 15 and 16 are schematic views of a histogram for describing region setting for counting the bacteria of every form by the bacteria analyzer 1 according to the second embodiment of the present invention.
Figure 16:
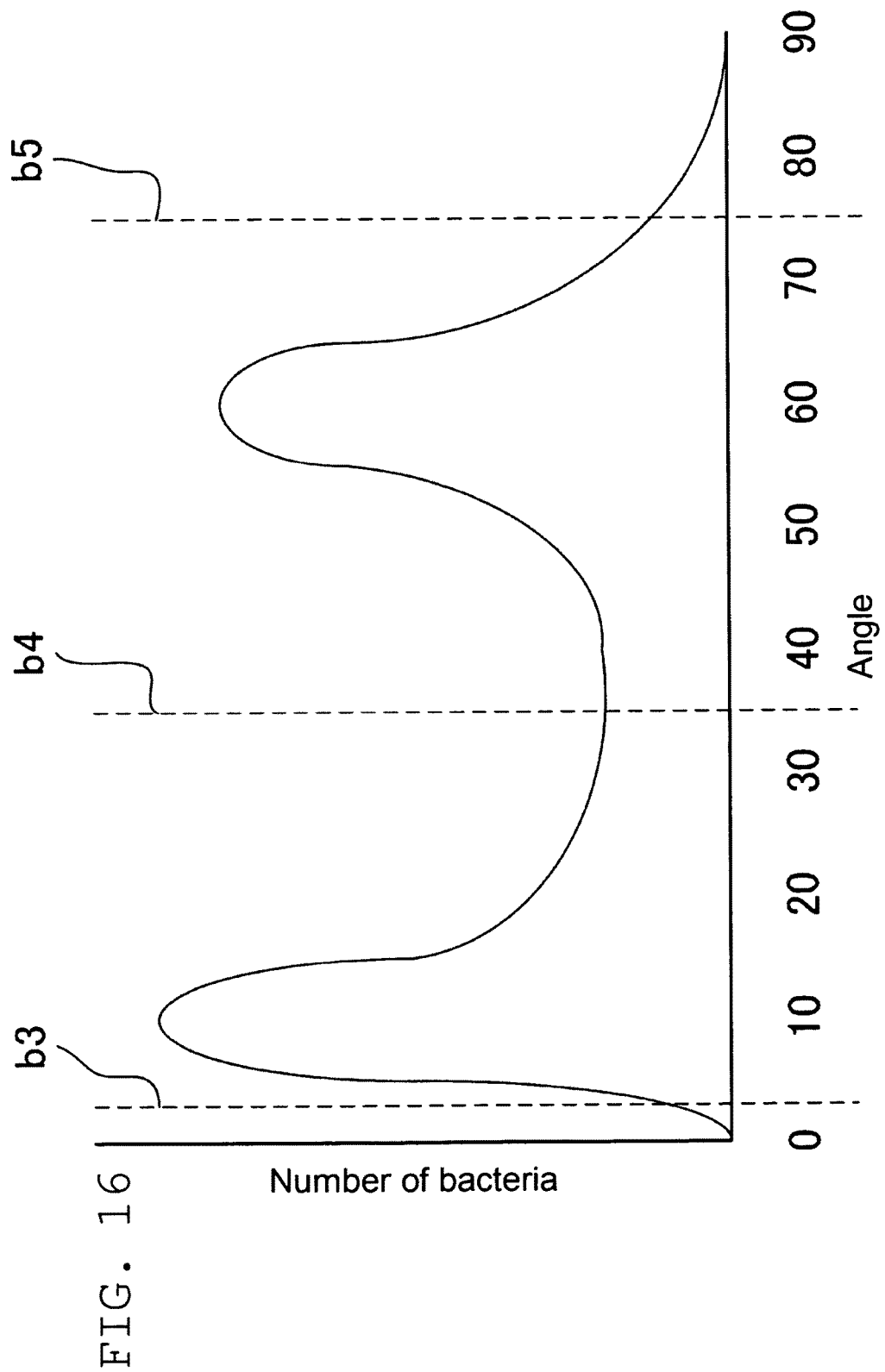

FIGS. 15 and 16 are views showing a variant of region setting in step S149. In this variant, the CPU 301a sets the region on the histogram obtained in step S155. For instance, if the histogram shown in FIG. 10 is obtained, the CPU 301a sets boundaries b1 and b2 shown in FIG. 15, and counts the bacteria within the region defined by the boundaries b1 and b2. The counted result indicates the number of bacteria belonging to the form determined in step S147. Similarly, if the histogram shown in FIG. 11 is obtained, the CPU 301a sets boundaries b3, b4 and b5 shown in FIG. 16, and counts the bacteria within the region defined by the boundaries b3 and b4 and the regions defined by the boundaries b4 and b5. The boundaries b1 to b5 may be fixed boundaries or the position may be changed depending on the obtained histogram.

Other Embodiments

In the bacteria analyzer 1 according to the first and the second embodiments, an example where the region B is not included in the regions D, D1, D2, D3, ... has been shown, but the present invention is not limited thereto. The regions D0, D1, D2, D3, ... may include the region B.

The bacteria analyzer 1 according to the first and the second embodiment shows an example of determining the rod-shaped bacteria, the chain coccus, and the staphylococcal as the form of bacteria, but the present invention is not limited thereto. The bacteria analyzer 1 may determine other forms of bacteria such as long rod-shaped bacteria and short rod-shaped bacteria.

In the bacteria analyzer 1 according to the first and the second embodiments, an example where the CPU 301a executes the processes of counting the bacteria and determining the form of bacteria has been shown, but the present invention is not limited thereto. For instance, the CPU 208 may execute such processes. In this case, the CPU 208 executes the processes of steps S142 to S148 (steps S152 to S160) after executing the measurement process in step S23 (see FIG. 5), and transmits the analysis result to the control device 3. The CPU 301a displays the received analysis result on the display unit 302 in step S15. An information processing device including a personal computer and the like connected to the measurement device 2 and the control device 3 by way of network may execute such processes. In this case, the CPU 208 transmits the measurement data to the information processing device in step S23 (see FIG. 5). After receiving the measurement data, the information processing device executes the processes of steps S141 to S148 (steps S151 to S160), and transmits the analysis result to the control device 3. The CPU 301a then displays the received analysis result on the display unit 302 in step S15.

In the bacteria analyzer 1 according to the first and the second embodiments, an example where the CPU 301a executes the process of creating the scattergram from the measurement data in step S142 (step S152) and executes the processes after step S143 by using such scattergram has been shown, but the present invention is not limited thereto. For instance, the CPU 301a may execute the process of reading out the measurement data from the hard disc 301d to the RAM 301c in step S141 (step S151), and then execute the processes after step S143 (step S153) based on the measurement data without creating the scattergram in step S142 (step S152).

What is claimed is:

1. A bacteria analyzer for analyzing bacteria contained in a specimen, comprising:
    a measurement device comprising:
        a light source for irradiating light on a measurement sample prepared from a specimen and a reagent; and
        a light receiving unit for receiving light generated by irradiating the light on the measurement sample from the light source; and
    a control device comprising a CPU and a non-transitory computer readable medium for storing a program, wherein the CPU is operable to execute the program to perform operations comprising:
        (a) acquiring scattergram data for generating a scattergram having information related to size of the bacteria contained in a specimen having a plurality of different forms of bacteria and fluorescence information generated by the bacteria as parameters, based on a signal obtained from the light received by the light receiving unit;
        (b) acquiring a number of bacteria contained in a plurality of regions on the scattergram for each region, based on the acquired scattergram data, the plurality of regions being radially divided into each region with an origin of the scattergram as a center;
        (c) acquiring a frequency distribution data for generating a frequency distribution graph which has as parameters, the number of bacteria in each region of the plurality of regions and distribution position of bacteria in each region of the plurality of regions, wherein the distribution position of bacteria comprises a radial angle of each region from the origin of the scattergram; and
        (d) determining a specific form of the bacteria contained in the specimen among the plurality of different forms of bacteria based on a region including a peak of the frequency distribution data, wherein the specific form of the bacteria and the radial angle of each region are associated based on experimental data and the CPU determines the specific form of the bacteria by the radial angle of the region having a peak number of bacteria.

2. The bacteria analyzer of claim 1, wherein each of the plurality of regions is a region excluding a predetermined region including an origin of the scattergram.

3. The bacteria analyzer of claim 1, wherein (d) determining the form of the bacteria further comprises determining a plurality of forms of the bacteria contained in the specimen, based on each region including each peak, when plural peaks exist in the frequency distribution graph.

4. The bacteria analyzer of claim 1, wherein (d) determining the form of the bacteria further comprises determining a plurality of forms of the bacteria contained in the specimen, based on the number of bacteria in each region acquired by the bacteria number acquirer.

5. The bacteria analyzer of claim 1, wherein (d) determining the form of the bacteria further comprises determining whether or not a rod-shaped bacteria is contained, whether or not a chain coccus is contained, or whether or not a staphylococcal is contained in the bacteria contained in the specimen.

6. The bacteria analyzer of claim 1, further comprising a sample preparing unit for preparing the measurement sample from the specimen and a fluorescence reagent for fluorescence staining the bacteria contained in the specimen, wherein
    the light receiving unit comprises:
        a scattered light receiving section for receiving a scattered light generated by irradiating light on the measurement sample; and
        a fluorescence receiving section for receiving fluorescence generated by irradiating light on the measurement sample.

* * * * *